United States Patent [19]

Laver

[11] Patent Number: Plant 7,136

[45] Date of Patent: Feb. 6, 1990

[54] ROSE PLANT — LAVGLO VARIETY

[75] Inventor: Keith Laver, Caledon East, Canada

[73] Assignee: The Conard-Pyle Company, West Grove, Pa.

[21] Appl. No.: 276,862

[22] Filed: Nov. 28, 1988

[51] Int. Cl.[4] ..... A01 5/00

[52] U.S. Cl. ..... Plt./8

[58] Field of Search ..... Plt. 8

*Primary Examiner*—Robert E. Bagwill

*Attorney, Agent, or Firm*—Burns, Doane, Swecker & Mathis

[57] ABSTRACT

A new and distinct variety of rose plant of the Miniature Class is provided which forms abundantly and continuously highly attractive double lemon yellow blossoms. The blossoms are long lasting and of good color stability. The plant is well suited for pot forcing and forms attractive ornamentation when grown as a flowering pot plant either indoors or outdoors.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the Rise 'N Shine variety (U.S. Plant Pat. No. 4,231). The male parent (i.e., the pollen parent) of the new variety was the Lemon Delight variety (non-patented in the United States). The parentage of the new variety can be summarized as follows:

Rise 'N Shine x Lemon Delight.

The seeds resulting from the above pollination were sown and small plantlets were obtained which were physically and biologically different from each other. Selective study resulted in the identification of a single plant of the new variety.

It was found that the new variety of Miniature rose plant of the present invention possesses the following combination of characteristics:

(a) forms in abundance on a continuous basis attractive long lasting double yellow blossoms which are of good color stability,
(b) exhibits a low, compact and well-branched growth habit, and
(c) is well suited for pot forcing.

The new variety well meets the needs of the horticultural industry for many usages. It is particularly well-suited for use as attractive ornamentation as a flowering pot plant for use indoors or outdoors.

The new variety has been found to undergo asexual propagation by a number of routes, including budding, grafting, cuttage, etc. The characteristics of the new variety have been found to be strictly transmissible by such asexual propagation from one generation to another.

The new variety has been named the Lavglo variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were six months of age and were observed during February while growing in a greenhouse at Cannet-des-Maures, Var, France.

FIG. 11 illustrates specimens of two flowering stems;

DETAILED DESCRIPTION

Figures 1, 2, 3, 4, 5, 6, 7, 8, 9, 10, 12, 13, 14, 15, 16:
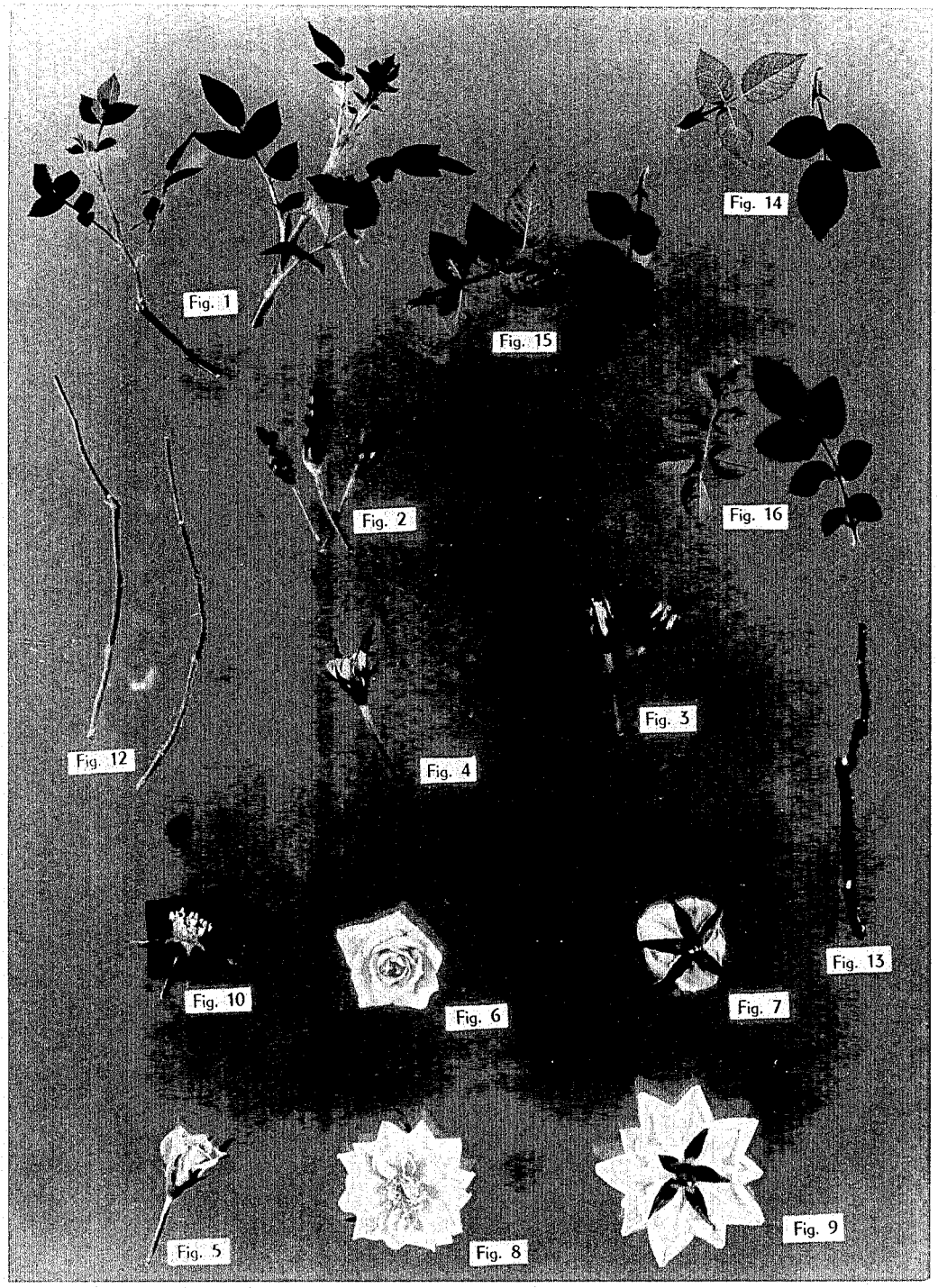
FIG. 1 illustrates specimens of two young shoots.
FIG. 2 illustrates specimens of three floral buds before the opening of the sepals.
FIG. 3 illustrates specimens of two floral buds at the opening of the sepals.
FIG. 4 illustrates a specimen of a floral bud at the opening of the petals.
FIG. 5 illustrates a specimen of a flower in the course of opening.
FIG. 6 illustrates a specimen of a flower — plan view — obverse.
FIG. 7 illustrates a specimen of a flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 12 illustrates a specimen of a main branch.
FIG. 13 illustrates specimens of leaves with three leaflets with the upper surface being shown on the right and the under surface being shown on the left.
FIG. 14 illustrates specimens of leaves with five leaflets with the upper surface being shown on the right and the under surface being shown on the left.
FIG. 15 illustrates specimens of leaves with seven leaflets with the upper surface being shown on the right and the under surface being shown on the left.

The chart used in the identification of the colors is that of The Royal Horticultural Society (R.H.S. Colour Chart). The terminology which precedes reference to the chart has been added to indicate the corresponding colors in common terms. The description is based on the observation of six month old specimens of the new variety during February while growing in a greenhouse at Cannet-des-Maures, Var, France.

Class: Miniature.
Plant:

*Height.*—Approximately 20 cm. on average.

*Habit.*—Bushy.

Branches:

*Color.*—Young stems: lettuce green, Yellow-Green Group 144A. Adult wood: medium green, Yellow-Green Group 146B.

*Thorns.*—Size: average. Quantity: few.

Leaves:

*Petioles.*—Upper surface: striped reddish brown on young wood and medium green with glandular edges on adult wood. Under surface: light green with a few tiny prickles.

*Stipules.*—Adnate, pectinate, narrow and linear.

*Leaflets.*—Number: 3, 5, and 7 (most often). Shape: elliptic. Serration: simple and regular. Texture: consistent. General appearance: dense semi-dual foliage. Color (young foliage): upper surface: medium green, Green Group 137C, stained with reddish coloration. Under surface: light green, Yellow-Green Group 148B. Color (adult foliage): upper surface: dark green, Yellow-Green Group 147A. Under surface: medium green, Yellow-Green Group 147B.

Inflorescence:

*Number of flowers.*—Usually 1 to 3 per stem.

*Peduncle.*—Straight, rigid, light green in coloration, its length is approximately 3 cm. on average.

*Sepals.*—Upper surface: tomentose, and greenish in coloration. Under surface: light green, the outer sepals have edges which are appendiculated.

*Buds.*—Shape: cone-shaped. Length: approximately 1.5 cm. on average. Size: average. Color upon opening: upper surface: aureolin, Yellow Group 12A. Under surface: aureolin, Yellow Group 12A.

*Flower.*—Form: as a cup, fully double. Diameter: approximately 3 cm. on average. Color: (when opening begins): upper surface: aureolin, Yellow Group 12A. Under surface: aureolin, Yellow Group 12A. Color (when blooming): upper surface: lemon yellow, Yellow Group 13A. Under surface: lemon yellow, Yellow Group 13A. Color (at end of opening): upper surface: barium yellow, Yellow Group 10A. Under surface: barium yellow, Yellow Group 10B. Fragrance: none. Lasting quality: long. Petal number: approximately 26 to 28 on average. Petal form: rounded with reversed edges on the sides. Petal texture: consistent. Petal drop: good. Anthers: straw yellow in coloration and edged with ochre yellow coloration above the stigma. Stamen number: approximately 70 on average. Filaments: normal, yellow in coloration, and of irregular heights. Pistil number: approximately 51 on average. Stigmas: straw yellow and greenish in coloration. Styles: free standing and of irregular heights. Receptacle: very light green in coloration and in longitudinal section is funnel-shaped.

Development:

*Vegetation.*—Vigorous.

*Blooming.*—Abundant and continuous.

*Resistance to Diseases.*—Normal.

I claim:

1. A new and distinct variety of Miniature rose plant characterized by the following combination of characteristics:

(a) forms in abundance on a continuous basis attractive long lasting double yellow blossoms of good color stability, (b) exhibits a low, compact and well-branched growth habit, and (c) is well suited for pot forcing;

substantially as herein shown and described, together with the parts thereof.

* * * * *